US012773544B1

(12) United States Patent
Vitello et al.

(10) Patent No.: US 12,773,544 B1
(45) Date of Patent: Oct. 27, 2026

(54) FLEX TEC CLOSURE ASSEMBLY FOR A MEDICAL DISPENSER

(71) Applicant: MEDICAL DEVICE ENGINEERING, LLC, Pompano Beach, FL (US)

(72) Inventors: Patrick Vitello, Pompano Beach, FL (US); Alexander Ollmann, Delray Beach, FL (US)

(73) Assignee: MEDICAL DEVICE ENGINEERING, LLC, Pompano Beach, FL (US)

( * ) Notice: Subject to any disclaimer, the term of this patent is extended or adjusted under 35 U.S.C. 154(b) by 424 days.

(21) Appl. No.: 18/239,704

(22) Filed: Aug. 29, 2023

Related U.S. Application Data

(63) Continuation of application No. 16/460,387, filed on Jul. 2, 2019, now Pat. No. 11,793,987.

(60) Provisional application No. 62/848,330, filed on May 15, 2019, provisional application No. 62/693,197, filed on Jul. 2, 2018.

(51) Int. Cl.

| | |
|---|---|
| ***A61M 39/10*** | (2006.01) |
| ***A61M 5/32*** | (2006.01) |
| *A61M 5/50* | (2006.01) |

(52) U.S. Cl.
CPC .......... *A61M 39/10* (2013.01); *A61M 5/3202* (2013.01); *A61M 5/3213* (2013.01); *A61M 5/3216* (2013.01); *A61M 5/5086* (2013.01)

(58) Field of Classification Search
CPC .. A61M 39/10; A61M 5/3202; A61M 5/3213; A61M 5/3216; A61M 5/5086; A61M 2005/3104; A61M 2005/312; A61M 2205/276; A61M 39/20; A61M 5/345; B65D 51/002; B65D 2251/0015; B65D 2251/009; B65D 51/18; B65D 41/46; B65D 41/3447; A61J 1/1412; A61J 1/1425
USPC ................................ 215/216, 228, 303, 295
See application file for complete search history.

(56) References Cited

U.S. PATENT DOCUMENTS

| | | | |
|---|---|---|---|
| 722,943 | A | 3/1903 | Chappell |
| 732,662 | A | 6/1903 | Smith |
| 1,678,991 | A | 7/1928 | Marschalek |

(Continued)

FOREIGN PATENT DOCUMENTS

| | | |
|---|---|---|
| CN | 110589435 | 12/2019 |
| DE | 202008018507 | 2/2015 |

(Continued)

OTHER PUBLICATIONS

Arai Tsugio, Pilfering Proof Cap, Jan. 9, 1996.

*Primary Examiner* — Wesley G Harris
(74) *Attorney, Agent, or Firm* — Malloy & Malloy, PL; Jennie S. Malloy; W. John Eagan

(57) ABSTRACT

A closure assembly for a medical dispenser including a cover and a tip cap removably disposed therein. A flexible retaining member including a plurality of flexible fingers is/are angularly positioned within the cover in both a retaining relation and a blocking position, which respectively restrict removal of the tip cap from the cover and a reinsertion of the tip cap, back into the cover, subsequent to its removal. Structurally distinguishable but similarly operable embodiments include the plurality of flexible fingers connected to and extending angularly outward from an interior of the cover or connected to an exterior of the tip cap.

14 Claims, 6 Drawing Sheets

(56) References Cited

U.S. PATENT DOCUMENTS 1,970,631 A 8/1934 Sherman
2,186,888 A 1/1940 Tullar et al.
2,277,936 A 3/1942 Rosenblatt
2,459,304 A 1/1949 Blank
2,477,598 A 8/1949 Hain
2,734,665 A 2/1956 Flamm
2,739,590 A 3/1956 Yochem
2,811,283 A 10/1957 Bowen
2,823,674 A 2/1958 Yochem
2,834,346 A 5/1958 Adams
2,875,761 A 3/1959 Helmer et al.
2,888,015 A 5/1959 Hunt
2,952,255 A 9/1960 Hein, Jr.
3,122,280 A 2/1964 Goda
3,180,532 A 4/1965 Michel
3,245,567 A 4/1966 Knight
3,301,256 A 1/1967 Cowley
3,323,798 A 6/1967 Miller
3,364,890 A 1/1968 Andersen
3,368,673 A 2/1968 Johnson
3,489,268 A 1/1970 Meierhoefer
3,568,673 A 3/1971 Cowley
3,574,306 A 4/1971 Alden
3,598,120 A 8/1971 Mass
3,610,241 A 10/1971 LeMarie
3,674,181 A 7/1972 Marks et al.
3,700,215 A 10/1972 Hardman et al.
3,706,307 A 12/1972 Hasson
3,710,922 A 1/1973 Lanphere et al.
3,712,749 A 1/1973 Roberts
3,726,445 A 4/1973 Ostrowsky et al.
3,730,325 A 5/1973 Goodwin
3,747,751 A 7/1973 Miller et al.
3,850,329 A 11/1974 Robinson
3,872,867 A 3/1975 Killinger
3,904,033 A 9/1975 Haerr
3,905,375 A 9/1975 Toyama
3,937,211 A 2/1976 Merten
3,987,930 A 10/1976 Fuson
4,005,739 A 2/1977 Winchell
4,027,669 A 6/1977 Johnston et al.
4,043,334 A 8/1977 Brown et al.
4,046,145 A 9/1977 Choksi et al.
4,068,696 A 1/1978 Winchell
4,085,845 A 4/1978 Perfect
4,106,621 A 8/1978 Sorenson
4,216,585 A 8/1980 Hatter
4,216,872 A 8/1980 Bean
4,220,151 A 9/1980 Whitney
4,244,366 A 1/1981 Raines
4,252,122 A 2/1981 Halvorsen
4,271,972 A 6/1981 Thor
4,286,591 A 9/1981 Raines
4,286,640 A 9/1981 Knox et al.
4,313,539 A 2/1982 Raines
4,369,781 A 1/1983 Gilson et al.
4,420,085 A 12/1983 Wilson et al.
4,430,077 A 2/1984 Mittleman et al.
4,433,790 A 2/1984 Gibson
4,457,445 A 7/1984 Hanks et al.
4,482,071 A 11/1984 Ishiwatari
D277,783 S 2/1985 Beck
4,520,942 A 6/1985 Dwinell
4,521,237 A 6/1985 Logothetis
4,530,697 A 7/1985 Kuhlemann et al.
4,558,554 A 12/1985 Herbert
4,571,242 A 2/1986 Klien et al.
4,589,171 A 5/1986 McGill
4,608,646 A 8/1986 Goodrich et al.
4,664,259 A 5/1987 Landis
4,667,837 A 5/1987 Vitello et al.
4,676,530 A 6/1987 Nordgren et al.
4,693,707 A 9/1987 Dye
4,726,483 A 2/1988 Drozd
4,735,617 A 4/1988 Nelson et al.
4,742,910 A 5/1988 Staebler
4,743,229 A 5/1988 Chu
4,743,231 A 5/1988 Kay et al.
4,744,455 A 5/1988 Dragotta et al.
4,753,345 A 6/1988 Goodsir et al.
4,760,847 A 8/1988 Vaillancourt
4,784,493 A 11/1988 Turcheck, Jr. et al.
4,813,564 A 3/1989 Cooper et al.
4,819,784 A 4/1989 Sticht
4,832,695 A 5/1989 Rosenberg et al.
4,834,706 A 5/1989 Beck et al.
4,842,592 A 6/1989 Caggiani et al.
4,844,906 A 7/1989 Hermelin et al.
4,863,451 A 9/1989 Marder
4,906,231 A 3/1990 Young
4,919,285 A 4/1990 Roof et al.
4,936,445 A 6/1990 Grabenkort
5,007,535 A 4/1991 Meseke et al.
5,009,323 A 4/1991 Montgomery et al.
5,024,323 A 6/1991 Bolton
5,049,129 A 9/1991 Zdeb et al.
5,057,093 A 10/1991 Clegg et al.
D323,392 S 1/1992 Bryne
5,078,696 A 1/1992 Nedbaluk
5,085,332 A 2/1992 Gettig et al.
5,090,564 A 2/1992 Chimienti
5,119,975 A 6/1992 Jemielita
5,133,454 A 7/1992 Hammer
5,135,496 A 8/1992 Vetter et al.
5,148,652 A 9/1992 Herzog
5,163,922 A 11/1992 McElveen, Jr. et al.
5,165,560 A 11/1992 Ennis, III et al.
5,230,429 A 7/1993 Etheredge, III
5,236,077 A 8/1993 Hoppmann et al.
5,267,983 A 12/1993 Oilschlager et al.
5,292,308 A 3/1994 Ryan
5,293,993 A 3/1994 Yates, Jr. et al.
5,295,599 A 3/1994 Smith
5,312,367 A 5/1994 Nathan
5,312,368 A 5/1994 Haynes
5,316,163 A 5/1994 von Schuckmann
5,328,466 A 7/1994 Denmark
5,328,474 A 7/1994 Raines
5,332,113 A 7/1994 Kusler, III et al.
5,356,380 A 10/1994 Hoekwater et al.
5,370,226 A 12/1994 Gollobin et al.
5,380,295 A 1/1995 Vacca
5,402,887 A 4/1995 Shillington
5,405,339 A 4/1995 Kohnen et al.
5,456,668 A 10/1995 Ogle, II
5,458,580 A 10/1995 Hajishoreh
5,468,224 A 11/1995 Souryal
5,474,178 A 12/1995 DiViesti et al.
5,484,413 A * 1/1996 Gevorgian .......... A61M 5/3213 604/110
5,505,705 A 4/1996 Galpin et al.
5,531,695 A 7/1996 Swisher
5,540,324 A 7/1996 Knapp
5,540,666 A 7/1996 Barta et al.
5,549,571 A 8/1996 Sak
5,558,648 A 9/1996 Shields
5,584,817 A 12/1996 van den Haak
5,588,239 A 12/1996 Anderson
5,611,445 A 3/1997 Kano et al.
5,617,954 A 4/1997 Kato et al.
5,624,402 A 4/1997 Imbert
5,662,233 A 9/1997 Reid
5,674,209 A 10/1997 Yarger
5,695,470 A 12/1997 Roussigne et al.
5,699,913 A 12/1997 Richardson
5,700,247 A 12/1997 Grimard et al.
5,702,374 A 12/1997 Johnson
5,706,985 A 1/1998 Feer
5,711,443 A 1/1998 Bennett
5,713,485 A 2/1998 Liff et al.
5,776,124 A 7/1998 Wald
5,785,691 A 7/1998 Vetter et al.
5,797,885 A 8/1998 Rubin
5,807,343 A 9/1998 Tucker et al.

(56) References Cited

U.S. PATENT DOCUMENTS 5,829,589 A 11/1998 Nguyen et al.
D402,766 S 12/1998 Smith et al.
5,842,567 A 12/1998 Rowe et al.
5,876,381 A 3/1999 Pond et al.
5,883,806 A 3/1999 Meador et al.
5,884,457 A 3/1999 Ortiz et al.
5,901,866 A 5/1999 Storar
5,902,269 A 5/1999 Jentzen
5,926,922 A 7/1999 Stottle
5,951,522 A 9/1999 Rosato et al.
5,951,525 A 9/1999 Thorne et al.
5,954,203 A 9/1999 Marconi
5,954,657 A 9/1999 Rados
5,957,166 A 9/1999 Safabash
5,957,314 A 9/1999 Nishida et al.
5,963,136 A 10/1999 O'Brien
5,983,596 A 11/1999 Corniani et al.
5,989,227 A 11/1999 Vetter et al.
5,993,437 A 11/1999 Raoz
6,000,548 A 12/1999 Tsals
D419,671 S 1/2000 Jansen
6,021,824 A 2/2000 Larsen et al.
6,027,482 A 2/2000 Imbert
6,068,614 A 5/2000 Kimber et al.
D430,293 S 8/2000 Jansen
6,112,951 A 9/2000 Mueller
D431,864 S 10/2000 Jansen
6,126,640 A 10/2000 Tucker et al.
6,190,364 B1 2/2001 Imbert
6,193,688 B1 2/2001 Balestracci et al.
6,196,593 B1 3/2001 Petrick et al.
6,196,998 B1 3/2001 Jansen et al.
6,216,885 B1 4/2001 Guillaume
6,235,376 B1 5/2001 Miyazaki et al.
6,279,746 B1 8/2001 Hussaini et al.
6,280,418 B1 8/2001 Reinhard et al.
6,287,671 B1 9/2001 Bright et al.
6,322,543 B1 11/2001 Singh et al.
6,325,227 B1 12/2001 Ekkert
6,338,200 B1 1/2002 Baxa et al.
6,358,241 B1 3/2002 Shapeton et al.
6,375,640 B1 4/2002 Teraoka
6,394,983 B1 5/2002 Mayoral et al.
6,439,276 B1 8/2002 Wood et al.
6,485,460 B2 11/2002 Eakins et al.
6,488,666 B1 12/2002 Geist
6,491,665 B1 12/2002 Vetter et al.
6,500,155 B2 12/2002 Sasso
6,520,935 B1 2/2003 Jansen et al.
6,540,697 B2 4/2003 Chen
6,565,529 B1 5/2003 Kimber et al.
6,581,792 B1 6/2003 Limanjaya
6,585,691 B1 7/2003 Vitello
6,592,251 B2 7/2003 Edwards et al.
6,666,852 B2 12/2003 Niedospial, Jr.
6,682,798 B1 1/2004 Kiraly
6,726,652 B2 4/2004 Eakins et al.
6,726,672 B1 4/2004 Hanly et al.
6,764,469 B2 7/2004 Broselow
6,796,586 B2 9/2004 Werth
6,821,268 B2 11/2004 Balestracci
D501,549 S 2/2005 McAllister et al.
6,921,383 B2 7/2005 Vitello
6,935,560 B2 8/2005 Andreasson et al.
6,942,643 B2 9/2005 Eakins et al.
6,961,638 B2 11/2005 Ouellette
6,991,126 B2 1/2006 Jackel
7,036,661 B2 5/2006 Anthony et al.
7,055,273 B2 6/2006 Roshkoff
7,100,771 B2 9/2006 Massengale et al.
7,125,397 B2 10/2006 Woehr et al.
7,141,286 B1 11/2006 Kessler et al.
7,175,081 B2 2/2007 Andreasson et al.
7,182,256 B2 2/2007 Andreasson et al.
7,232,066 B2 6/2007 Anderasson et al.
7,240,926 B2 7/2007 Dalle et al.
7,258,222 B2 8/2007 Marti Sala et al.
7,299,981 B2 11/2007 Hickle et al.
7,367,964 B2 5/2008 Heinz et al.
7,374,555 B2 5/2008 Heinz et al.
7,404,500 B2 7/2008 Marteau et al.
7,410,803 B2 8/2008 Nollert et al.
7,425,208 B1 9/2008 Vitello
7,437,972 B2 10/2008 Yeager
7,438,704 B1 10/2008 Kawashima et al.
D581,046 S 11/2008 Sudo
D581,047 S 11/2008 Koshidaka
D581,049 S 11/2008 Sudo
7,482,166 B2 1/2009 Nollert et al.
D589,612 S 3/2009 Sudo
7,497,330 B2 3/2009 Anthony et al.
7,503,453 B2 3/2009 Cronin et al.
7,588,563 B2 9/2009 Guala
7,594,681 B2 9/2009 DeCarlo
7,608,057 B2 10/2009 Woehr et al.
7,611,487 B2 11/2009 Woehr et al.
7,632,244 B2 12/2009 Buehler et al.
D608,900 S 1/2010 Giraud et al.
7,641,636 B2 1/2010 Moesli et al.
D612,939 S 3/2010 Boone, III et al.
7,681,606 B2 3/2010 Khan et al.
7,698,180 B2 4/2010 Fago et al.
7,708,035 B2 5/2010 Windmiller
7,735,664 B1 6/2010 Peters et al.
7,748,892 B2 7/2010 McCoy
7,762,988 B1 7/2010 Vitello
7,766,919 B2 8/2010 Delmotte
7,802,313 B2 9/2010 Czajka
7,886,908 B2 2/2011 Farrar et al.
7,918,830 B2 4/2011 Langan et al.
7,922,213 B2 4/2011 Werth
7,988,004 B1 8/2011 Marret et al.
8,034,041 B2 10/2011 Domkowski et al.
8,079,518 B2 12/2011 Turner et al.
8,091,727 B2 1/2012 Domkowwski
8,118,788 B2 2/2012 Frezza
8,120,484 B2 2/2012 Chisholm
8,128,605 B2 3/2012 Masi et al.
8,137,324 B2 3/2012 Bobst
8,140,349 B2 3/2012 Hanson et al.
8,151,970 B2 4/2012 McDonald et al.
8,231,585 B2 7/2012 Heinz et al.
8,252,247 B2 8/2012 Ferlic
8,257,286 B2 9/2012 Meyer et al.
8,328,082 B1 12/2012 Bochenko et al.
8,348,895 B1 1/2013 Vitello
8,353,869 B2 1/2013 Ranalletta et al.
8,413,410 B2 4/2013 Ulm et al.
8,413,811 B1 4/2013 Arendt
8,443,999 B1 5/2013 Reinders
D684,057 S 6/2013 Kwon
8,512,277 B2 8/2013 Del Vecchio
8,528,757 B2 9/2013 Bisio
8,556,074 B2 10/2013 Turner et al.
8,579,116 B2 11/2013 Pether et al.
8,591,462 B1 11/2013 Vitello
8,597,255 B2 12/2013 Emmott et al.
8,597,271 B2 12/2013 Langan et al.
8,616,413 B2 12/2013 Koyama
D701,304 S 3/2014 Lair et al.
8,672,902 B2 3/2014 Ruan et al.
8,702,674 B2 4/2014 Bochenko
8,777,910 B2 7/2014 Bauss et al.
8,777,930 B2 7/2014 Swisher et al.
8,813,944 B2 8/2014 Tanner
8,852,561 B2 10/2014 Wagner et al.
8,864,021 B1 10/2014 Vitello
8,864,707 B1 10/2014 Vitello
8,864,708 B1 10/2014 Vitello
8,911,424 B2 12/2014 Weadock et al.
8,945,082 B2 2/2015 Geiger et al.
8,978,909 B2 3/2015 Kakutani et al.
8,985,305 B2 3/2015 Wong et al.
9,016,473 B2 4/2015 Tamarindo

(56) References Cited

U.S. PATENT DOCUMENTS 9,027,769 B2 5/2015 Willows et al.
9,082,157 B2 7/2015 Gibson
9,095,667 B2 8/2015 Schuckman
9,101,534 B2 8/2015 Bochenko
D738,495 S 9/2015 Strong et al.
9,125,976 B2 9/2015 Uber, III et al.
D743,019 S 11/2015 Schultz
9,192,443 B2 11/2015 Tennican
9,199,042 B2 12/2015 Farrar et al.
9,199,749 B1 12/2015 Vitello et al.
9,220,486 B2 12/2015 Schweiss et al.
9,220,577 B2 12/2015 Jessop et al.
9,227,019 B2 1/2016 Swift et al.
D750,228 S 2/2016 Strong et al.
9,272,099 B2 3/2016 Limaye et al.
9,311,592 B1 4/2016 Vitello et al.
D756,777 S 5/2016 Berge et al.
9,336,669 B2 5/2016 Bowden et al.
D759,486 S 6/2016 Ingram et al.
D760,384 S 6/2016 Niunoya et al.
D760,902 S 7/2016 Persson
9,402,967 B1 8/2016 Vitello
9,427,715 B2 8/2016 Palazzolo et al.
9,433,768 B2 9/2016 Tekeste et al.
9,463,310 B1 10/2016 Vitello
D773,043 S 11/2016 Ingram et al.
9,480,801 B2 11/2016 Schiller et al.
D777,903 S 1/2017 Schultz
9,662,456 B2 5/2017 Woehr
D789,529 S 6/2017 Davis et al.
9,687,249 B2 6/2017 Hanlon et al.
9,694,948 B1 7/2017 Pakhomov et al.
9,744,304 B2 8/2017 Swift et al.
D797,928 S 9/2017 Davis et al.
D797,929 S 9/2017 Davis et al.
9,764,098 B2 9/2017 Hund et al.
9,821,152 B1 11/2017 Vitello et al.
D806,241 S 12/2017 Swinney et al.
D807,503 S 1/2018 Davis et al.
9,855,191 B1 1/2018 Vitello et al.
D815,945 S 4/2018 Fischer
9,987,438 B2 6/2018 Stillson
D825,746 S 8/2018 Davis et al.
10,039,913 B2 8/2018 Yeh et al.
D831,201 S 10/2018 Holtz et al.
D834,187 S 11/2018 Ryan
10,124,122 B2 11/2018 Zenker
10,166,343 B1 1/2019 Hunt et al.
10,166,347 B1 1/2019 Vitello
10,183,129 B1 1/2019 Vitello
10,207,099 B1 2/2019 Vitello
10,207,835 B2 2/2019 Wilhelm et al.
D842,464 S 3/2019 Davis et al.
D847,373 S 4/2019 Hurwit et al.
10,293,987 B2 5/2019 Sattig et al.
10,300,263 B1 5/2019 Hunt
10,307,548 B1 6/2019 Hunt et al.
10,315,024 B1 6/2019 Vitello et al.
10,315,808 B2 6/2019 Taylor et al.
10,376,655 B2 8/2019 Pupke et al.
D859,125 S 9/2019 Weagle et al.
10,478,262 B2 11/2019 Niese et al.
10,555,872 B1 2/2020 Thorne
10,618,711 B2 4/2020 Weir
10,695,490 B2 6/2020 Perazzo et al.
10,758,684 B1 9/2020 Vitello et al.
10,759,611 B1 9/2020 Kalm
10,773,067 B2 9/2020 Davis et al.
10,800,556 B2 10/2020 Thorne et al.
D903,865 S 12/2020 Banik et al.
10,888,672 B1 1/2021 Vitello
10,898,659 B1 1/2021 Vitello et al.
10,912,898 B1 2/2021 Vitello et al.
10,933,202 B1 3/2021 Banik
10,940,087 B2 3/2021 Thorne et al.
10,953,162 B1 3/2021 Hunt et al.
11,040,149 B1 6/2021 Banik
11,040,154 B1 6/2021 Vitello et al.
11,065,181 B2 * 7/2021 Davis .................... A61J 1/2096
11,097,071 B1 8/2021 Hunt et al.
11,168,818 B2 11/2021 Fangrow
11,254,514 B2 2/2022 Vienot et al.
11,278,681 B1 3/2022 Banik et al.
D948,713 S 4/2022 Banik
11,357,588 B1 6/2022 Vitello et al.
11,413,406 B1 8/2022 Vitello et al.
11,426,328 B1 8/2022 Ollmann et al.
11,471,610 B1 10/2022 Banik et al.
11,523,970 B1 12/2022 Vitello et al.
11,541,180 B1 1/2023 Vitello et al.
11,690,994 B1 7/2023 Banik et al.
11,697,527 B1 7/2023 Hendren et al.
11,779,520 B1 10/2023 Vitello
11,793,987 B1 10/2023 Vitello et al.
11,850,210 B2 12/2023 Dadachanji et al.
11,857,751 B1 1/2024 Vitello
11,872,187 B1 1/2024 Vitello et al.
11,904,149 B1 2/2024 Vitello et al.
11,911,339 B1 2/2024 Lehel et al.
12,070,591 B1 8/2024 Vitello
12,172,803 B1 12/2024 Vitello et al.
12,195,241 B1 1/2025 Vitello et al.
12,201,230 B2 1/2025 Bell
12,383,463 B1 8/2025 Vitello et al.
12,478,449 B1 11/2025 Vitello et al.
12,545,483 B1 2/2026 Vitello et al.
12,702,623 B1 8/2026 Vitello et al.
12,708,723 B1 8/2026 Banik et al.
2001/0003150 A1 6/2001 Imbert
2001/0034506 A1 10/2001 Hirschman et al.
2001/0041866 A1 * 11/2001 Capes ................... A61M 5/348
604/110
2001/0056258 A1 12/2001 Evans
2002/0007147 A1 1/2002 Capes et al.
2002/0023409 A1 2/2002 Py
2002/0046962 A1 4/2002 Vallans et al.
2002/0079281 A1 6/2002 Hierzer et al.
2002/0097396 A1 7/2002 Schafer
2002/0099334 A1 7/2002 Hanson et al.
2002/0101656 A1 8/2002 Blumenthal et al.
2002/0104770 A1 8/2002 Shapeton et al.
2002/0133119 A1 9/2002 Eakins et al.
2002/0188259 A1 12/2002 Hickle et al.
2003/0041560 A1 3/2003 Kemnitz
2003/0055685 A1 3/2003 Cobb et al.
2003/0146617 A1 8/2003 Franko, Sr.
2003/0183547 A1 10/2003 Heyman
2003/0187403 A1 10/2003 Balestracci
2004/0008123 A1 1/2004 Carrender et al.
2004/0011623 A1 1/2004 Sala
2004/0064095 A1 4/2004 Vitello
2004/0116858 A1 6/2004 Heinz et al.
2004/0129738 A1 7/2004 Stukas
2004/0173563 A1 9/2004 Kim et al.
2004/0186437 A1 9/2004 Frenette et al.
2004/0225258 A1 11/2004 Balestracci
2005/0146081 A1 7/2005 MacLean et al.
2005/0148941 A1 7/2005 Farrar et al.
2005/0209555 A1 9/2005 Middleton et al.
2006/0049948 A1 3/2006 Chen et al.
2006/0084925 A1 4/2006 Ramsahoye
2006/0089601 A1 4/2006 Dionigi
2006/0169611 A1 8/2006 Prindle
2006/0173415 A1 8/2006 Cummins
2006/0189933 A1 8/2006 Alheidt et al.
2007/0060898 A1 3/2007 Shaughnessy et al.
2007/0106234 A1 5/2007 Klein
2007/0142786 A1 6/2007 Lampropoulos et al.
2007/0191690 A1 8/2007 Hasse et al.
2007/0219503 A1 9/2007 Loop et al.
2007/0257111 A1 11/2007 Ortenzi
2008/0068178 A1 3/2008 Meyer
2008/0078146 A1 4/2008 Cirio
2008/0097310 A1 4/2008 Buehler et al.

(56) References Cited

U.S. PATENT DOCUMENTS

2008/0106388 A1 5/2008 Knight
2008/0140020 A1 6/2008 Shirley
2008/0243088 A1 10/2008 Evans
2008/0302711 A1 12/2008 Windmiller
2008/0303267 A1 12/2008 Schnell et al.
2008/0306443 A1 12/2008 Neer
2009/0008356 A1 1/2009 Gadzic et al.
2009/0062744 A1* 3/2009 Weilbacher ........... A61M 5/158 604/192
2009/0084804 A1 4/2009 Caspary et al.
2009/0099552 A1 4/2009 Levy et al.
2009/0149815 A1 6/2009 Kiel et al.
2009/0166311 A1 7/2009 Claessens
2009/0212954 A1 8/2009 Adstedt et al.
2009/0326481 A1 12/2009 Swisher et al.
2010/0050351 A1 3/2010 Colantonio et al.
2010/0051491 A1 3/2010 Lampropoulos et al.
2010/0084403 A1 4/2010 Popish et al.
2010/0089862 A1 4/2010 Schmitt
2010/0126894 A1 5/2010 Koukol et al.
2010/0179822 A1 7/2010 Reppas
2010/0211016 A1 8/2010 Palmer-Felgate
2010/0228226 A1 9/2010 Nielsen
2010/0252564 A1* 10/2010 Martinez .............. A21C 15/005 220/796
2010/0283238 A1 11/2010 Deighan et al.
2010/0307108 A1 12/2010 Sink et al.
2011/0009836 A1 1/2011 Chebli et al.
2011/0044850 A1 2/2011 Solomon et al.
2011/0046550 A1 2/2011 Schiller et al.
2011/0046603 A1 2/2011 Felsovalyi et al.
2012/0064515 A2 3/2012 Knapp et al.
2012/0096957 A1 4/2012 Ochman
2012/0110950 A1 5/2012 Schraudolph
2013/0018356 A1 1/2013 Prince et al.
2013/0018536 A1 1/2013 Prince et al.
2013/0037383 A1 2/2013 Iwasa et al.
2013/0056130 A1 3/2013 Alpert et al.
2013/0088354 A1 4/2013 Thomas
2013/0145725 A1 6/2013 Bianco et al.
2013/0237949 A1 9/2013 Miller
2013/0269592 A1 10/2013 Heacock et al.
2014/0000781 A1 1/2014 Franko, Jr.
2014/0034536 A1 2/2014 Reinhardt et al.
2014/0069202 A1 3/2014 Fisk
2014/0069829 A1 3/2014 Evans
2014/0076840 A1 3/2014 Graux et al.
2014/0135738 A1 5/2014 Panian
2014/0155868 A1 6/2014 Nelson et al.
2014/0163465 A1 6/2014 Bartlett, II et al.
2014/0257843 A1 9/2014 Adler et al.
2014/0319141 A1 10/2014 Stratis et al.
2014/0326727 A1 11/2014 Jouin et al.
2014/0353196 A1 12/2014 Key
2014/0358078 A1 12/2014 Fischer et al.
2015/0013811 A1 1/2015 Carrel et al.
2015/0048045 A1 2/2015 Miceli et al.
2015/0112296 A1 4/2015 Ishiwata et al.
2015/0136632 A1 5/2015 Moir et al.
2015/0182686 A1 7/2015 Okihara
2015/0191633 A1 7/2015 De Boer et al.
2015/0246185 A1 9/2015 Heinz
2015/0251820 A1 9/2015 Glaser et al.
2015/0298414 A1 10/2015 Dittmer et al.
2015/0302232 A1 10/2015 Strassburger et al.
2015/0305982 A1 10/2015 Bochenko
2015/0310771 A1 10/2015 Atkinson et al.
2016/0067144 A1 3/2016 Chang
2016/0067422 A1 3/2016 Davis et al.
2016/0090456 A1 3/2016 Ishimaru et al.
2016/0136352 A1 5/2016 Smith et al.
2016/0144119 A1 5/2016 Limaye et al.
2016/0158110 A1 6/2016 Swisher et al.
2016/0158449 A1 6/2016 Limaye et al.
2016/0176550 A1 6/2016 Viitello et al.
2016/0194121 A1 7/2016 Ogawa et al.
2016/0250420 A1 9/2016 Maritan et al.
2016/0279032 A1 9/2016 Davis
2016/0328586 A1 11/2016 Bowden et al.
2016/0361235 A1 12/2016 Swisher
2016/0367439 A1 12/2016 Davis et al.
2017/0007771 A1 1/2017 Duinat et al.
2017/0014310 A1 1/2017 Hyun et al.
2017/0124289 A1 5/2017 Hasan et al.
2017/0173321 A1 6/2017 Davis et al.
2017/0203086 A1 7/2017 Davis
2017/0225843 A1 8/2017 Glaser et al.
2017/0239141 A1 8/2017 Davis et al.
2017/0297781 A1 10/2017 Kawamura
2017/0319438 A1 11/2017 Davis et al.
2017/0328758 A1 11/2017 Fuchs
2017/0349335 A1 12/2017 Sattig et al.
2017/0354792 A1 12/2017 Ward
2018/0001540 A1 1/2018 Byun
2018/0014998 A1 1/2018 Yuki et al.
2018/0064604 A1 3/2018 Drmanovic
2018/0078684 A1 3/2018 Peng et al.
2018/0089593 A1 3/2018 Patel et al.
2018/0098915 A1 4/2018 Rajagopal et al.
2018/0147115 A1 5/2018 Nishioka et al.
2018/0236177 A1 8/2018 Schraga
2018/0312305 A1 11/2018 Rognard
2019/0275313 A1 9/2019 Godin et al.
2019/0308006 A1 10/2019 Erekovcanski et al.
2019/0388626 A1 12/2019 Okihara
2021/0228445 A1 7/2021 Bouteloup et al.
2021/0244892 A1 8/2021 Maritan et al.
2021/0362910 A1 11/2021 Morgan
2022/0008645 A1 1/2022 Ukai et al.
2022/0024630 A1 1/2022 Bohamed
2022/0257467 A1 8/2022 Yano et al.
2022/0296470 A1 9/2022 Wagner
2022/0339067 A1 10/2022 Christine et al.
2023/0036805 A1 2/2023 Rey

FOREIGN PATENT DOCUMENTS

DE 102020123373 3/2020
DE 102020123392 3/2022
DE 102020131870 6/2022
EP 0148116 7/1985
EP 269920 6/1988
EP 571980 12/1993
EP 2724977 4/2014
EP 2937616 A1 * 10/2015 ............ A61M 39/10
GB 486367 6/1938
GB 2102774 2/1983
JP 08002544 1/1996
JP 2014076618 5/2014
KR 101159987 6/2012
KR 101868822 6/2018
WO WO8607040 12/1986
WO WO9118801 12/1991
WO WO1992003348 3/1992
WO WO2008000279 1/2008
WO WO2017086607 5/2015
WO WO-2025003684 A1 * 1/2025 ............ A61J 1/1475

* cited by examiner

FLEX TEC CLOSURE ASSEMBLY FOR A MEDICAL DISPENSER

CLAIM OF PRIORITY

The present application is a Continuation patent application of and claims priority to a previously filed, currently U.S. Non-Provisional patent application, namely, that having Ser. No. 16/460,387, and a filing date of Jul. 2, 2019, and further, claims priority pursuant to 35 U.S.C. Section 119(e) to a prior filed Provisional patent application, namely, that having Ser. No. 62/693,197 filed on Jul. 2, 2018, and to another Provisional patent application filed on May 15, and having Ser. No. 62/848,330, the contents of which are all incorporated herein by reference in their entireties.

BACKGROUND OF THE INVENTION

Field of the Invention

This invention is directed to a closure assembly for a medical dispenser including a cover and a tip cap removably disposed therein. A flexible retaining member may be disposed within the cover in different positions which respectively retain the tip cap within the cover and prevent reinsertion thereof, subsequent to its removal from the cover.

Description of the Related Art

In the medical field, it is a common procedure for authorized medical personnel to order medicine or other substances to be administered to a patient whether orally, by an injection or intravenously through an IV. It is also a relatively common procedure for a number of administering devices, such as a syringe, to be pre-filled by authorized personnel whether within the hospital or at another filling station. However, such a filling station is typically located in a remote part of the facility, relative to the patient care area, where the injection is to be administered. Because of the remote location of many nurse's stations, relative to a filling station, a fluid or drug loaded syringe or other medical device is frequently given to another person for delivery to a nurse's station for subsequent dosing of the patient. In the case where a prefilled drug in the syringe is very expensive or addictive such as, but not limited to, morphine, there is a danger of tampering, by a person seeking unauthorized access to the prefilled contents of the syringe or medical device.

If tampering does occur, the potential for serious consequences exists. For example, there is a possibility that the prescribed medicine will be replaced by some other, unauthorized substance. As an illustration of this, if saline solution were substituted for a dose of morphine or other medication, the result could be extremely serious. Thus, there is a problem of knowing if a sealed, pre-loaded syringe or other administering device has, or has not, been compromised by tampering and/or exposed to contamination so that it is no longer sterile.

In addition to the administration of drugs, medicine, etc., meaningful protection is required in the use of enteral feeding sets. As commonly recognized in the medical and related professions, the term "enteral" relates to the administration or removal of fluid to or from the gastrointestinal tract. Moreover, enteral connectors and/or fixtures of the type referred to herein relate to medical devices or accessories which are intended for use in enteral applications. Further, small-bore connectors for enteral application may be employed for delivery of enteral nutrition fluid from a fluid source to the patient. Additionally, it is pointed out that enteral feeding sets and extension sets may include a female fixture, wherein the source of fluid flows to the patient initially through the female fixture and to and through a cooperatively structured male enteral fixture.

Also, with regard to administering fluids to a patient by intravenous (IV) infusion, a variety of IV assemblies are used in the treatment of numerous medical conditions. Different types of connectors, such as a "female" connector may be attached to the discharge end or discharge port of an IV bag or like medical device/container. Such an appropriate female connector may be in the form of a female Luer connector which at least partially defines, along with a male Luer connector, a "Luer lock" connector assembly, as is well known in the medical profession. In periods of non-use, it is important to maintain such connectors associated with an IV facility, in a closed and fluid sealed condition in order to maintain sterility and integrity of the IV fluid prior to use.

Therefore, regardless of the known or conventional attempts to provide a fluid restricting closure to protect the contents of preloaded medical dispensers or administering devices including enteral devices, certain problems still remain in this field of art. Accordingly, there is a need in this area for an improved, closure assembly which provides a secure and reliable, fluid restricting or fluid sealing connection to the discharge port, fixture or connector of a medical device of the type set forth herein. If any such improved closure assembly were developed, it would preferably also overcome known disadvantages in the production and/or assembly of conventional closures, including tamper evident closures.

However, in order to do so, any such closure assembly would preferably also include a unique construction to help reduce, if not eliminate, the need for time-consuming, costly and overly complicated production techniques associated with the production of more conventional closures for medical devices. Also, if any such closure assembly were developed, it should further be capable of use with little or no structural modification on a variety of different connectors, fixtures, administering devices, discharge ports, etc.

Finally, if any such improved closure assembly were developed, it should also be structurally and operatively reliable, while improving the cost effectiveness associated with the manufacture and assembly thereof.

SUMMARY OF THE INVENTION

The present invention is directed to a closure assembly for a medical connector including a cover having an access opening, a hollow interior communicating with the access opening, and a closed end disposed opposite to the access opening. A tip cap is disposed within the cover and includes a flow restrictor disposed in communicating relation with the access opening of the cover. The tip cap is structured to establish a frictional, diametric interference fit and fluid sealing connection with the discharge port of the medical dispenser.

As used herein the term "discharge port" is meant to include the structure, section, segment, portion and/or component of the medical dispenser through which the contents of the dispenser pass, upon exiting the medical dispenser in the conventional manner. By way of non-limiting example and as represented herein, the medical dispenser may be in the form of, but not be limited to, a syringe, including a prefilled syringe. Moreover, when the medical dispenser is in the form of a prefilled syringe, the discharge port is meant to include, but not necessarily be limited to, a nozzle, a flow channel within the nozzle and a terminal opening formed in the outer end of the nozzle, through which the contents of the syringe pass upon exiting the interior thereof.

As indicated, at least one embodiment of the flow restrictor of the tip cap is structured to establish a frictional, removal resistant, fluid sealing connection with the discharge port of the medical dispenser. As explained in greater detail hereinafter, the fluid sealing connection determines and/or defines a removal force capable of concurrently removing the tip cap and the medical dispenser, when the discharge port and flow restrictor are attached. The removal force is established by creating a pulling force on the medical dispenser, exterior of the cover and/or concurrently on both. Further, due to the frictionally resistant fluid sealing connection, the removal force will be greater than a retaining force, serving to retain the tip cap within the cover.

In more specific terms, the present invention further includes a flexible retaining member, at least initially disposed within the cover in a retaining relation to the tip cap and between the tip cap and the cover. Such a removable retaining relation restricts removal of the tip cap from the interior of the cover, until the aforementioned removal force is exerted on the medical dispenser and/or cover, resulting in a concurrent removal of the tip cap and the discharge port connected thereto.

The flexible retaining member comprises in a preferred embodiment, a plurality of flexible material fingers disposed in spaced relation to one another and angularly oriented between the tip cap and the interior of the cover. In different embodiments of the present invention, the angular orientation of the flexible material fingers varies. However, in each embodiment they are initially disposed in a retaining relation, which restricts removal of the tip cap from the interior of the cover. Further, each of a possible plurality of embodiments include the positioning and/or orientation of the flexible material fingers in a "blocking position", which prevents reinsertion of the tip cap into the interior of the cover, once it has been removed therefrom. As a result, attempted tampering or authorized access to the contents of the medical dispenser will be evident.

Accordingly, one embodiment of the present invention includes the plurality of flexible fingers, defining the flexible retaining member, having a proximal end fixedly attached to the interior surface of the cover, in spaced relation to one another and extending angularly outward therefrom. The plurality of flexible fingers are all disposed in a predetermined angular orientation, which in this embodiment is preferably an acute angular orientation relative to the interior surface of the cover, to which they are attached. As a result, the plurality of flexible material fingers include a plurality of free ends, correspondingly disposed in a substantially collectively aligned position. While the number of fingers may vary, preferably they are sufficient in number to collectively extend in an open, substantially circular or continuous curvilinear configuration about the interior surface of the cover and may be generally in the range of 20 in number.

It is to be noted that the flexible material from which the plurality of fingers are formed is such as to maintain their fixed attachment to the cover upon the concurrent removal of the tip cap and the connected discharge port. Such a fixed positioning and connection allows for the disposition of the plurality of fingers in the aforementioned "blocking position", which in turn, restricts reinsertion of the tip cap once it has been removed from the cover. The fixedly attached, flexible structuring of the plurality of fingers has the advantage of remaining intact before and after removal of the tip cap from the cover, upon the exertion of a removal force thereon. This provides an advantage over more conventional, frangible or removable retaining structures, by limiting the possibility of any broken parts or pieces remaining in the cover and/or tip cap upon a breakage of a frangible or other removable connection.

Further, in each of the embodiments of the present invention the plurality of fingers are preferably made of a ductile material such as, but not limited to, polypropylene. As such, the plurality of fingers are designed to flex rather than break, thereby limiting the aforementioned possibility of loose pieces or parts, after normal use. Also, the retention force exerted on the tip cap is established somewhat utilizing the principal associated with the deflection of multiple cantilever beams. In accordance therewith, upon removal of the tip cap through the plurality of flexible fingers, it will naturally follow the path of least resistance, as it passes through the plurality of fingers, out of the cover. By way of example only, if one or more of the fingers were significantly stiffer than the others, the tip cap will naturally move to the side of the cover corresponding to the more flexible fingers. The increased force associated with the "stiff fingers" is thereby at least partially mitigated, while maintaining a preferred or intended retaining force on the tip cap.

Therefore, in the embodiment defined by the plurality of flexible material fingers being fixedly attached to the cover, the retaining relation is defined by the plurality of fingers disposed in surrounding, movement interrupting relation to the tip cap, as they are positioned between the tip cap and the access opening of the cover. The aforementioned "retaining force" is determined by the degree of flexibility of the plurality of fingers and is overcome by a superior "removal force" exerted on the attached medical dispenser and/or exterior of the cover when they are pulled apart.

In turn, the aforementioned blocking position of the plurality of flexible fingers is defined by their disposition in the acute angle relative to the interior surface of the cover, as they extend angularly outward there from, at least generally towards the access opening. In such a "blocking position," the free ends are disposed in interruptive engagement with portions of the tip cap as it passes through the access opening of the cover in an attempt to reinsert the tip cap into its original position, prior to removal. The inability to reinsert the tip cap in the cover will be evidence of tampering or authorized use.

Yet another embodiment of the present invention the retainer is defined by the plurality of flexible material fingers being fixedly attached to an exterior of the tip cap and extending angularly outward therefrom. Preferably, the angular outwardly extending orientation of the plurality of flexible material fingers relative to the tip cap is defined by an obtuse angle. Therefore, as originally assembled, the plurality of fingers include their proximal ends fixedly attached to the tip cap and the oppositely disposed free ends disposed in retaining engagement with interior surface portions of the cover.

However, subsequent to a concurrent removal of the tip cap and a discharge port connected thereto, the free ends of the plurality of flexible material fingers will be disposed in blocking engagement with portions of the interior surface of the cover, upon an attempted reentry of the tip cap, into the cover. Further, prevention of the reinsertion of the tip cap into the cover may be further facilitated by the provision of an obstruction integrally or otherwise fixedly formed on the interior surface of the cover in interruptive relation to the free ends of the fingers, as the tip cap passes through the access opening, in a reentry attempt.

As with the previously described embodiment, it is to be noted that the flexible, preferably ductile material from which the plurality of fingers are formed is such as to maintain their fixed attachment to the tip cap after the concurrent removal of the tip cap and connected discharge port from the cover. Such a fixed positioning and connection to the tip cap allows for the disposition of the plurality of fingers in the aforementioned "blocking position", which in turn, restricts reinsertion of the tip cap once it has been removed from the cover. The fixedly attached, flexible structuring of the plurality of fingers has the advantage of remaining intact over more conventional frangible or removable retaining structures, as set forth in detail herein.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
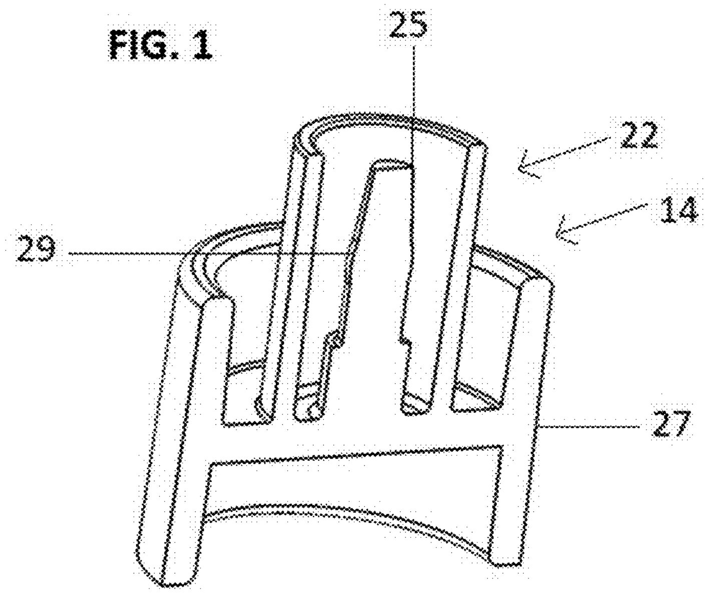
FIG. 1 is a perspective interior sectional view of a tip cap component of the closure assembly of the present invention.

As represented in the accompanying Figures the present invention is directed a closure assembly for a medical dispenser, generally represented as 10 and 10' in different embodiments of the present invention. Moreover, and as perhaps best shown in FIGS. 2, and 5-7, each of the embodiments of the closure assembly 10 and 10' includes a cover 12 and 12' and a cooperatively structured tip cap 14 and 14'. Further, each of the covers 12 and 12' include an access opening 16 and an oppositely disposed closed end 18 collectively defining boundaries of a hollow interior 20. Also, the tip cap 14 and 14' of each closure assembly 10 and 10' includes a flow restrictor 22 and 22' with each flow restrictor 22 and 22' disposed in communicating relation with the access opening 16 of the respective cover 12 and 12'. In at least one embodiment, the flow restrictor 22 of the tip cap 14 is structured to be operatively disposed and establish a "diametric interference fit" and/or frictional, fluid sealing connection with the discharge port 100 of the medical dispenser. However, and as explained hereinafter, the discharge ports 100 of each of the different embodiments of a medical dispenser useable with the present invention may be modified and/or specifically structured to define the fluid sealing connection by means of the aforementioned "diametric interference fit" and/or by a threaded engagement, thereby demonstrating the versatility of the closure assembly 10, 10' of the present invention.

Figure 4:
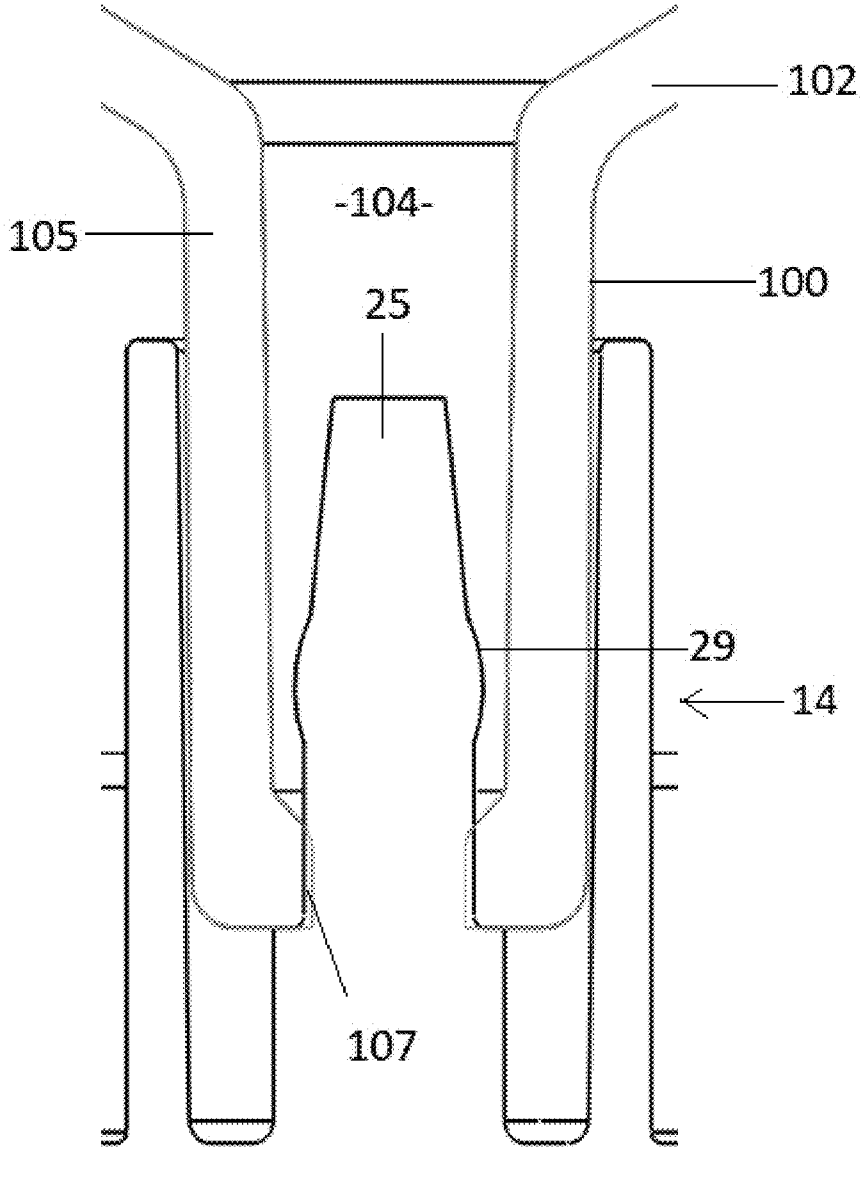
FIG. 4 is a detailed sectional view in partial cutaway of a frictional attachment between the medical dispenser and the tip cap of the embodiment of FIG. 1.

For purposes of clarity, the term "discharge port", as used herein, is meant to describe and include the structure, section, segment, portion and/or component of the medical dispenser through which the contents of the medical dispenser pass, upon removal from the interior thereof. By way of non-limiting example, and as represented herein, the medical dispenser may be in the form of, but not be limited to, a syringe, including a prefilled syringe. Moreover, and as shown in FIG. 4, when the medical dispenser 102 is in the form of a prefilled syringe, the discharge port 100 is meant to include, but not necessarily be limited to, a nozzle 105, a flow channel 104 within the nozzle 105 and a terminal opening 107 formed in the outer end of the nozzle 105, through which the contents of the syringe pass upon exiting the interior of the medical dispenser/syringe 102.

Figure 2:
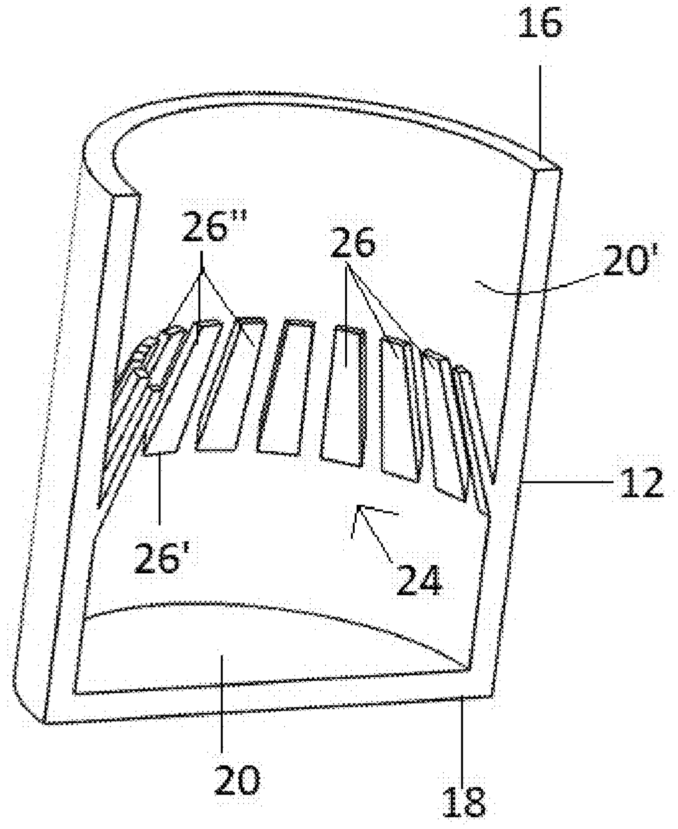
FIG. 2 is a perspective interior sectional view of a cover component of the closure assembly of the present invention.
Figure 3:
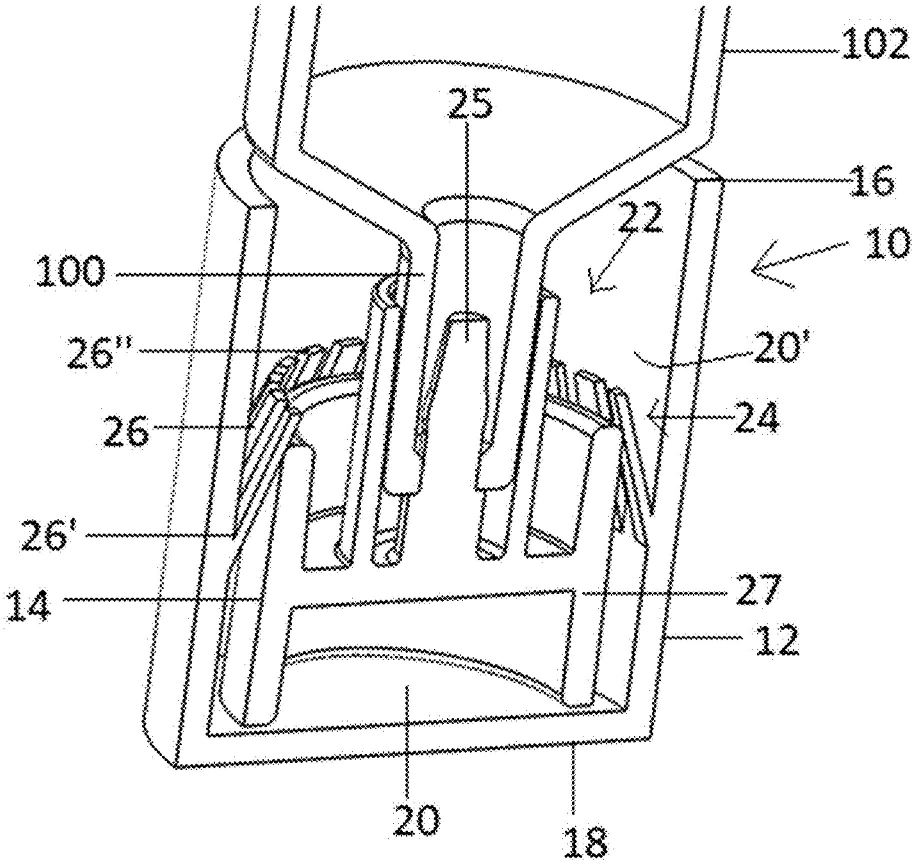
FIG. 3 is a perspective interior sectional view of the assembled components of the embodiments of FIGS. 1 and 2 operatively disposed in connection to a medical dispenser.

As indicated hereinafter, the different embodiments of the closure assembly 10, 10' may include different structural features, but also include a commonality of operation in the form of a flexible retaining member 24 and 24' as best shown in FIGS. 2 and 3. Further, the flexible retaining member 24 and 24' is/are positioned within the respective cover 12 and 12', between the tip cap 14 and 14' and interior surface portions 20' of the cover 12 and 12', in retaining relation to the tip cap 14 and 14'. In addition, the flexible retaining member 24 and 24' of each of the embodiments of the closure assembly 10 and 10' may be disposed in a "blocking position" which prevents reentry of the tip cap 14 and 14', into the interior 20 of the cover 12 and 12', after it has been removed therefrom.

Still referring to FIGS. 2 and 3, each flexible retaining member 24 and 24' is illustrated as comprising a plurality of flexible material fingers 26 disposed in spaced relation to one another and angularly oriented between the respective tip cap 14 and 14' and the interior surface 20' of the cover 12 and 12'. In different embodiments of the present invention, the angular orientation of the flexible material fingers 26 varies. However, in each embodiment, the plurality of flexible material fingers 26 are initially disposed in a retaining relation or position. Further, the retaining relation or position of each embodiment is such as to restrict removal of the tip cap 14 and 14' from the interior 20 of the cover 12 and 12'. Further, each of a possible plurality of embodiments include the positioning and/or orientation of the flexible material fingers 26 in a "blocking position", which prevents reinsertion of the tip cap 14 and 14' into the interior 20 of the cover 12 and 12', once it has been removed therefrom.

Therefore, and with reference now to FIGS. 1-4, one embodiment of the closure assembly 10 of the present invention comprises the cover 12 including an access opening or open end 16, oppositely disposed closed end 18 and hollow interior 20. The tip cap 14 includes the flow restrictor having a sealing stem 25, described in greater detail with primary reference to FIG. 4. In addition, the tip cap 14 includes an outer, substantially surrounding skirt 27 having a preferred and predetermined dimension which facilitates its passage through the access opening 16 of the cover 12.

Figure 5:
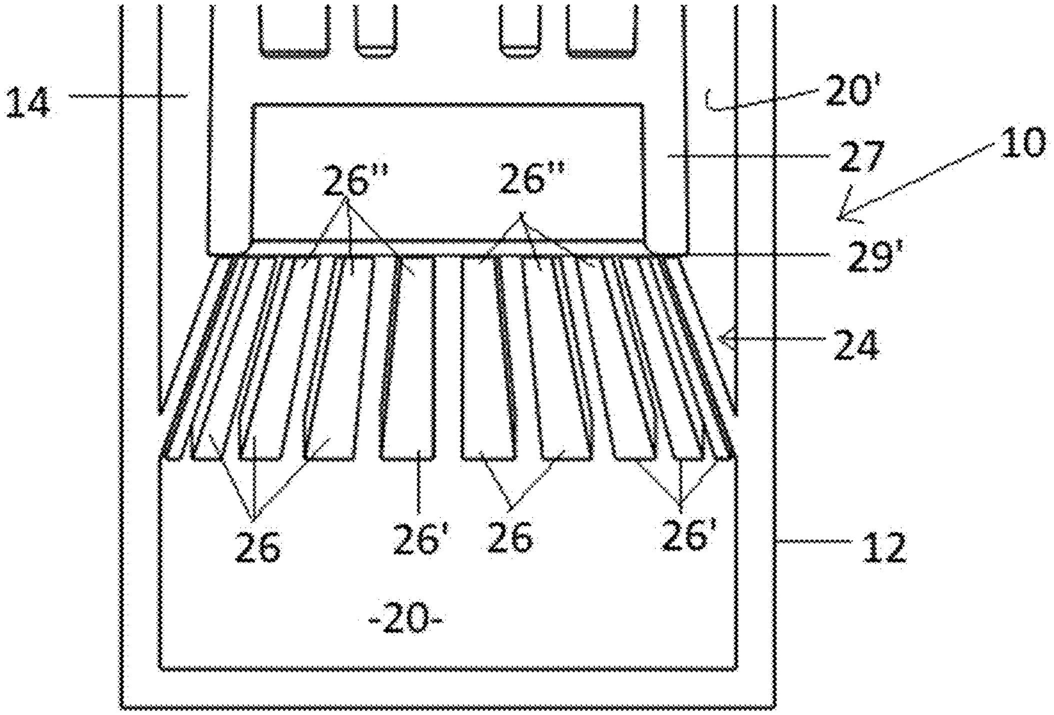
FIG. 5 is an interior sectional view in partial cutaway representing an attempted reinsertion of the tip cap into the cover, subsequent to the removal thereof.

As represented in FIGS. 2, 3 and 5, the flexible retaining member 24 comprises a plurality of flexible material fingers 26 having their proximal end 26' fixedly connected to the interior surface 20' of the cover 12. Further, each of the plurality of flexible material fingers 26 is/are disposed in spaced relation to one another and extend angularly outward from the interior surface 20' to a terminating free end 26". In this embodiment, the angular orientation of the plurality of fingers 26 relative to the interior surface 20' may be substantially common and will preferably define an acute angular orientation. As a result, the free ends 26" are correspondingly disposed in substantially aligned relation to one another, in a substantially circular or other curvilinear array, as represented in FIGS. 2, 3 and 5.

FIG. 3 is representative of the flexible retaining member 24 and plurality of flexible retaining FIG. 26 being disposed in the aforementioned retaining position or relation to the tip cap 14. As such, the plurality of flexible material fingers 26 are disposed in substantially surrounding relation to the tip cap 14 and/or the skirt 27 and may be disposed in direct retaining engagement therewith. In such a retaining position or relation, the plurality of flexible fingers 26 exert a retaining force on the tip cap 14, thereby restricting or preventing its removal from the interior 20 of the cover inadvertently during handling, shipping, etc. However, once attached in the fluid engaging connection with the discharge port 100, by virtue of the frictional, “diametric interference fit” with the sealing stem 25, a sufficient pulling or removal force can be exerted on the medical dispenser or the exterior of the cover 12 or both.

With reference now to FIG. 4, the fluid sealing connection between the flow restrictor 22 and the discharge port 100 is accomplished by insertion of the sealing stem 25 into the interior of the flow channel 104 of the discharge port 100. As indicated, the sealing stem 25 has a retention bump or bulbous portion 29 formed thereon, substantially intermediate opposite ends of the sealing stem 25. This retention bump 29 allows the syringe nozzle 105 and more particularly, the terminal opening 107 to flex over and slip beyond the retention bump 29 into a relaxed normally configured orientation, once the terminal opening 107 passes beyond the retention bump 29. The cooperative dimensions of the terminal opening 107 and the retention bump 29 is such that a sufficient pulling or removal force may be exerted on the medical dispenser 102, in order to remove the tip cap 14 and the discharge port 100 from the interior 20 of the cover 12.

Therefore, the frictional, fluid sealing connection between the discharge port 100 and the tip cap 14, via the sealing stem 25 of the discharge port 22, will allow a removal force to be exerted on the tip cap 14, once connected to the discharge port 100. Accordingly, the fluid sealing connection between the discharge port 100 and the tip cap 14, via the sealing stem 25, defines or determines a “removal force” which is greater than the retaining force, exerted on the tip cap 14 by the plurality of flexible material fingers 26. As a result, exertion of the pulling force on the tip cap 14 will not result in a separation of the tip cap 14 and the discharge port 100, since the removal force is sufficient to “overcome” the retaining force.

As described, the removal force is determined and defined by the frictional, fluid sealing connection between the sealing stem 25 and the discharge port 100. However, as will be explained in greater detail with reference to FIGS. 6 and 7, a flow restrictor incorporated within a tip cap may be differently structured to establish a fluid sealing connection with a variety of different discharge ports. As a result, the fluid sealing connection may be established and defined by structures other than the sealing stem 25 and retention bump 29.

FIG. 5 is a representation of the tip cap 14 having been removed from the interior 20 of the cover 12 and an attempt to reinsert the tip cap 14. Therefore, the flexible retainer 24, specifically including the plurality of flexible material fingers 26, is represented as being disposed in a “blocking position” in order to prevent reinsertion of the tip cap 14. In more specific terms, the free ends 26" of the plurality of flexible material fingers 26 are disposed in interruptive, blocking engagement with the inner terminal end 29' of the skirt 29 of the tip cap 14. As set forth above, the diameter of the skirt 29 has a predetermined dimension allowing it to pass through the access opening 16 of the cover 12, but coming into engagement with the correspondingly disposed and aligned free ends 26" of the plurality of flexible material fingers 26, upon attempted reinsertion thereof, as represented in FIG. 5.

As represented, the angular orientation of the plurality of flexible material fingers 26 is such that the correspondingly disposed, substantially aligned orientation of the free ends 26" is smaller than the outer diameter of the access opening 16. The plurality of correspondingly positioned free ends 26" are disposed and structured to substantially correspond to the diameter of the terminal end of the skirt 27. As a result, the angularly oriented plurality of flexible material fingers 26 are disposed in the aforementioned “blocking position” by virtue of their free ends 26" disposed in interruptive engagement with the skirt 27.

Figure 6:
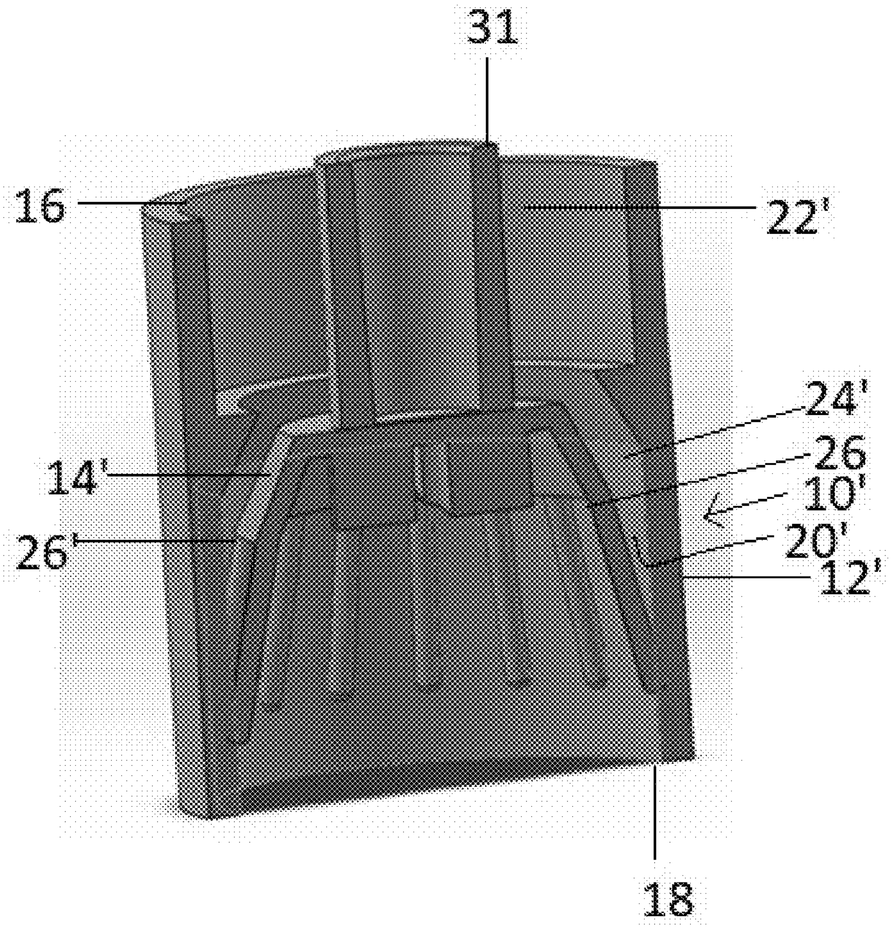
FIG. 6 is a perspective interior sectional view of another embodiment of the closure assembly of the present invention.
Figure 7:
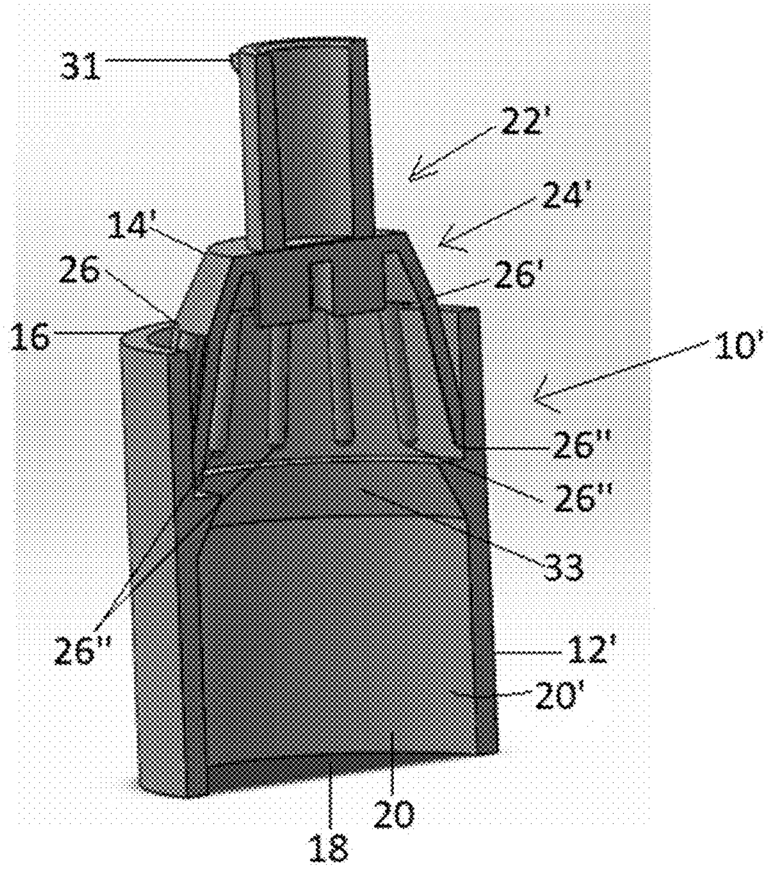
FIG. 7 is a perspective interior sectional view of the embodiment of FIG. 6 representing an attempted reinsertion of a tip cap into a cover, subsequent to the removal thereof.

Yet another embodiment of the closure assembly 10' is generally represented in FIGS. 6 and 7. As indicated the distinguishing structural features of this embodiment, as compared to the embodiment of FIGS. 1-5, includes the position and orientation of the plurality of flexible material fingers 26 defining the flexible retaining member 24'. As such, the plurality of fingers 26 include their proximal ends 26' integrally or fixedly connected to a generally exterior portion of the tip cap 14' and/or flow restrictor 22'. Further, the plurality of flexible fingers 26 extend angularly outward from the tip cap 14' in an obtuse angular relative to the flow restrictor 22. In cooperation therewith, the plurality of flexible fingers 26 are disposed within the interior 20 of the cover 12 and are disposed at a substantially acute angle to the interior surface 20' of the cover 12.

As represented in FIG. 6, the tip cap 14' is disposed within the interior 20 of the cover 16 as originally assembled. When so disposed, the plurality of flexible fingers 26 are disposed in a retaining relation to the tip cap by their retaining engagement with the interior surface portions 20' of the cover 12. As a result, a retaining force is developed, which may be exerted on the tip cap 14' and which is sufficient to prevent or restrict inadvertent removal of the tip cap 14' from the cover during shipping, handling, etc.

In a practical application, the flow restrictor 22' is connected to a discharge port of a medical dispenser (not represented in FIGS. 6 and 7). The versatility of the closure assembly 10 and 10' is demonstrated by the different structuring of the flow restrictor 22', as compared to the flow restrictor 22 of the embodiments of FIGS. 1-5. Further, the flow restrictor 22' is structured to be attached to a cooperatively structured discharge port using a threaded attachment to establish the fluid sealing connection therebetween. Therefore, an outer end of the flow restrictor 22' may have at least one outwardly projecting rib or thread structure 31. The rib or thread structure 31 is disposed, dimensioned and configured to establish a threaded attachment to a cooperatively structured internally threaded discharge port, to thereby define the fluid sealing connection therebetween. When so connected, a removal force can be exerted on the tip cap 14' by exerting a pulling force on the connected discharge port, or on the cover 12 or both. Such a pulling force will result in the exertion of the aforementioned removal force on the tip cap 14'. Such a generated removal force, established by the fluid sealing connection between the discharge port and the flow restrictor 22', will be greater than the retaining force exerted on the tip cap 14' by the plurality of fingers 26. As a result, the tip cap 14' will be concurrently removed from the interior 20 of the cover 12' along with the attached discharge port.

FIG. 7 is representative of the tip cap 14' passing through the access opening 16 of the cover 12' in an attempt to reinsert it into the interior 20 of the cover 12'. However, due to the angular orientation of the plurality of flexible fingers 26, extending outwardly from the tip cap 14', the free ends 26" will come into interruptive engagement with an interior surface portion of the cover 12', such as an internal surface obstruction 33. The internal surface obstruction 33 is preferably integrally or fixedly formed on the interior surface 20' in a substantially elongated, curvilinear rib or like structure. As such, the internal surface obstruction 33 extends outwardly from the interior surface 20', towards the interior center of the cover 12'. As a result of such interruptive engagement between the interior surface obstruction 33 and the free ends 26" of the fingers 26, the tip cap 14' will be prevented from reentry into the interior 20 of the cover 12', into its original position when assembled.

What is claimed is:

1. A closure assembly for a medical dispenser comprising:
- a cover including an access opening and a hollow interior,
- a tip cap removably disposed within said cover and including a flow restrictor,
- said flow restrictor structured for a fluid sealing connection with a discharge port of the medical dispenser,
- said fluid sealing connection defining a removal force sufficient to concurrently remove said tip cap and the discharge port from said cover,
- a flexible retaining member positioned within said cover between said tip cap and said cover and in a retaining engagement with said tip cap,
- said flexible retaining member structured to define a predetermined retaining force determinative of maintenance of said tip cap within said cover, concurrent to said retaining engagement with said tip cap,
- said flexible retaining member comprises a plurality of flexible material fingers disposed in spaced relation to one another and in substantially surrounding relation to said tip cap,
- said flow restrictor and said flexible retaining member cooperatively structured to define said removable force being greater than said predetermined retaining force,
- said flexible retaining member further disposed in a blocking position relative to a reinsertion of said tip cap within said hollow interior of said cover, subsequent to said concurrent removal of said tip cap and the discharge port from said cover, and
- said plurality of fingers are fixedly connected to an interior surface of said cover and extending angularly outward therefrom, into said retaining engagement and said blocking position.

2. The closure assembly as recited in claim 1 wherein said plurality of fingers are disposed in a predetermined angular orientation relative to said tip cap and said cover.

3. The closure assembly as recited in claim 2 wherein said predetermined angular orientation defines disposition of said flexible retaining member in said retaining engagement and said blocking position.

4. The closure assembly as recited in claim 1 wherein said plurality of fingers include correspondingly positioned free ends collectively disposed in said blocking position.

5. The closure assembly as recited in claim 4 wherein said blocking position comprises said correspondingly positioned free ends disposed in interruptive relation to said tip cap concurrent to passage thereof into said cover, through said access opening.

6. A closure assembly for a medical dispenser comprising:
- a cover including an access opening and a hollow interior,
- a tip cap including a flow restrictor removably disposed within said cover,
- said flow restrictor structured for fluid sealing connection with a discharge port of the medical dispenser,
- a retaining member comprising a plurality of flexible fingers including proximal ends fixedly connected to an interior surface of said cover,
- said plurality of flexible fingers extending angularly outward from said proximal ends, in spaced relation to one another and in retaining engagement with said tip cap,
- said retaining engagement comprising said plurality of flexible fingers disposed in substantially surrounding, interruptive relation to said tip cap, between said access opening and said tip cap, and
- said plurality of flexible fingers formed of a sufficiently flexible material to allow concurrent removal of said tip cap and a connected discharge port, upon a predetermined removal force being exerted on said tip cap.

7. The closure assembly as recited in claim 6 wherein said plurality of flexible fingers are disposed angularly outward from said interior surface of said cover at an acute angle.

8. The closure assembly as recited in claim 7 wherein said plurality of fingers include correspondingly disposed free ends collectively disposed in a blocking position.

9. The closure assembly as recited in claim 8 wherein said blocking position comprises said correspondingly disposed free ends positioned in interruptive engagement with said tip cap concurrent to insertion of said tip cap through said access opening.

10. The closure assembly as recited in claim 6 wherein each of said plurality of fingers include a free end, each of said free ends disposed in a blocking position.

11. The closure assembly as recited in claim 10 wherein said blocking position comprises each of said free ends positioned in interruptive engagement with said tip cap concurrent to insertion of said tip cap through said access opening.

12. A closure assembly for a medical dispenser comprising:
- a cover including an access opening and a hollow interior,
- a tip cap removably disposed within said cover and including a flow restrictor,
- said flow restrictor structured for a fluid sealing connection with a discharge port of the medical dispenser,
- said fluid sealing connection defining a removal force sufficient to concurrently remove said tip cap and the discharge port from said cover,
- a flexible retaining member including a plurality of flexible fingers, each of said flexible fingers including a proximal end and a free end,
- each of said proximal ends fixedly connected to an interior surface of said cover and said plurality of fingers extending angularly outward from said interior surface into substantially surrounding and retaining engagement with said tip cap,
- said plurality of flexible fingers structured to define a predetermined retaining force determinative of removable maintenance of said tip cap within said cover, concurrent to said retaining engagement with said tip cap, said flow restrictor and said plurality of flexible fingers cooperatively structured to define said removable force being greater than said predetermined retaining force, said flexible retaining member further disposed in a blocking position relative to a reinsertion of said tip cap within said hollow interior of said cover, subsequent to said concurrent removal of said tip cap and the discharge port from said cover, and said blocking position comprising said free ends disposed in interruptive relation to said tip cap concurrent to passage thereof into said cover, through said access opening.

13. The closure assembly as recited in claim 12 wherein said plurality of fingers are disposed in a predetermined angular orientation relative to said tip cap and said cover.

14. The closure assembly as recited in claim 13 wherein said predetermined angular orientation defines disposition of said flexible retaining member in said retaining engagement and said blocking position.

* * * * *